United States Patent [19]

Eggensperger et al.

[11] 4,129,517

[45] Dec. 12, 1978

[54] AQUEOUS PEROXY-CONTAINING CONCENTRATE

[75] Inventors: Heinz Eggensperger, Hamburg; Wolfgang Beilfuss, Hamburg-Hummelsbüttel, both of Germany

[73] Assignee: Sterling Drug Inc., New York, N.Y.

[21] Appl. No.: 855,461

[22] Filed: Nov. 28, 1977

[30] Foreign Application Priority Data

Nov. 30, 1976 [DE] Fed. Rep. of Germany ....... 2654164

[51] Int. Cl.$^2$ ....................... C11D 3/395; C11D 7/18; A61K 33/40; C11D 7/54

[52] U.S. Cl. ........................................ 252/186; 8/111; 252/102; 260/502 R; 568/559; 423/272; 424/130; 424/338

[58] Field of Search .................... 252/186, 95, 99, 102; 8/111; 260/502 A, 502 R, 610 A; 423/272, 273; 424/130, 338

[56] References Cited

U.S. PATENT DOCUMENTS

| | | | |
|---|---|---|---|
| 2,820,821 | 1/1958 | Guest et al. | 260/502 A |
| 3,130,169 | 4/1964 | Blumbergs et al. | 252/186 |
| 3,168,554 | 2/1965 | Phillips et al. | 260/502 R |

*Primary Examiner*—Benjamin R. Padgett

*Assistant Examiner*—Irwin Gluck

*Attorney, Agent, or Firm*—Frederik W. Stonner; B. Woodrow Wyatt

[57] ABSTRACT

A stable aqueous peroxy-containing concentrate containing by weight of the concentrate 1 to 60 percent of perglutaric acid; 1 to 50 percent of hydrogen peroxide; 0.01 to 2 percent of a stabilizing agent for the perglutaric acid and hydrogen peroxide; and the remainder to 100 percent water.

3 Claims, No Drawings

AQUEOUS PEROXY-CONTAINING CONCENTRATE

BACKGROUND OF THE INVENTION

1. Field of the Invention

The invention relates to stable, aqueous concentrates of perglutaric acid useful in the preparation of aqueous bleach, detergent and antimicrobial compositions.

2. Description of the Prior Art

It is known that percarboxylic acids are excellent oxidizing and disinfecting agents. It also is known that lower aliphatic percarboxylic acids, such as peracetic acid and perpropionic acid, can form stable solutions with a high peracid content. These peracids, however, have a very pungent odor, which makes their handling difficult and even hazardous. A further considerable disadvantage of peracetic acid is its relatively high volatility, which in addition to resulting in an annoying odor, leads to an undesirable uptake in man, animals and plants through inhalation and resorption and could preclude its use on toxicological grounds.

It would be highly desirable therefore if stable, aqueous percarboxylic acid solutions containing relatively high concentrations of percarboxylic acid could be prepared which could be diluted with water for ultimate use and which would be odorless or have only a slight odor.

Percarboxylic acids, which have little odor and which are water soluble exist in the class of lower dicarboxylic acids. Thus, maleic acid and succinic acid form practically odorless, water soluble peracids. However, stable solutions of high peracid content cannot be prepared from these peracids. Thus, when persuccinic acid is prepared from succinic anhydride and hydrogen peroxide, the initial high content of persuccinic acid decreases upon extended storage. Furthermore, the decomposition of persuccinic acid leads to crystallization of the resulting succinic acid. The solubility of peradipic acid in water is too low to permit the preparation of solutions of adequate peracid content. Aqueous solutions of perdiglycolic acid can be prepared but the peracid content of such solutions is too low. There is therefore a need for a solution of a technical problem of long standing, namely, the preparation of stable, nearly odorless, aqueous peracid concentrates which markedly improve and simplify the handling of organic per-compounds not only as disinfectants but also in oxidation and bleaching processes. Concentrated solutions in the field of peracids are desirable since dilute peracid solutions are not stable, and hence, cannot be marketed.

SUMMARY OF THE INVENTION

Surprisingly, it has now been discovered that perglutaric acid, which is nearly odorless, practically non-volatile and very water-soluble, can be formulated as a stable aqueous concentrate of markedly higher peracid content than its adjacent homologs, persuccinic acid and peradipic acid, and other closely related peracids such as maleic acid.

Thus the invention provides a stable, aqueous peroxy-containing concentrate consisting essentially of by weight of the concentrate:

(a) about 1 to 60 percent of perglutaric acid;

(b) about 1 to about 50 percent of hydrogen peroxide;

(c) about 0.01 to about 2 percent of a stabilizing agent for the perglutaric acid and the hydrogen peroxide; and (d) the remainder to 100 percent water.

The perglutaric acid concentrates of the invention have high stability and hence can be stored for extended periods of time. Moreover, these concentrates, because of their high perglutaric acid content, can be substantially diluted to provide solutions having excellent oxidizing properties.

DETAILED DESCRIPTION INCLUSIVE OF THE PREFERRED EMBODIMENTS

The perglutaric acid content of the peroxy-containing concentrate of the invention can range from about 1 to 60 percent by weight of the concentrate, and the hydrogen peroxide content can range from about 1 to 50 percent by weight of the concentrate, and preferably from about 5 to 30 percent by weight of the concentrate. When the concentration of the perglutaric acid falls in the lower portion of the 1 to 60 percent range, i.e., about 1 to 20 percent, the concentration of the hydrogen peroxide should be about 10 to 50 percent and preferably 20 to 50 percent by weight of the concentrate. At higher concentrations of perglutaric acid, lower concentrations of hydrogen peroxide can be employed.

It is surprising that stable, aqueous solutions of 1 to 60 weight-percent of perglutaric acid can be prepared since similar stable, aqueous solutions with peracid concentrations falling within this weight-percent range cannot be obtained from the next lower and higher homologs of perglutaric acid, namely, peradipic acid and persuccinic acid. In the case of peradipic acid, its solubility is too low to provide solutions of the desired high concentration. Thus if one attempts to prepare peradipic acid by mixing 5 parts of adipic anhydride and 95 parts of 35% hydrogen peroxide, a clear solution cannot be obtained. In the case of persuccinic acid on the other hand, aqueous solutions having a weight-percent concentration over 8 percent can be prepared but the concentration of the persuccinic acid decreases fairly rapidly, even in the presence of a stabilizing agent, and crystallization and precipitation of succinic acid results.

Perdiglycolic acid solutions can be prepared but such solutions also have a peracid content which is too low. Thus, addition of 10 parts of diglycolic anhydride to 90 parts of 35% hydrogen peroxide yields a clear, colorless, odorless solution. However, on standing for one day, the solution assays for only 2.26% perdiglycolic acid. If the reaction is repeated in the presence of 0.2% stabilizing agent, a clear solution results which assays for only 2.74% perdiglycolic acid.

Similarly, the investigations of a large number of additional organic peracids of low odor, such as the peracids of oxalic acid, malonic acid, lactic acid, methoxyacetic acid, ethoxyacetic acid, citric acid, acetylcitric acid and sorbic acid, never led to the extraordinarily favorable results obtained with perglutaric acid.

As stabilizing agent for the peroxy-containing concentrate of the invention, any stabilizer for hydrogen peroxide can be employed. Such stabilizers are well known and are, for example, urea, pyridine N-oxide, 2,3-pyridine-dicarboxylic acid, 2,6-pyridinedicarboxylic acid and mixtures of 2,3- and 2,6-pyridinedicarboxylic acid, pyrophosphates and phytic acid. The stabilizing agent should be present in the concentrate in about 0.01 to 2 percent by weight of the concentrate and preferably about 0.05 to 0.5 weight-percent.

The pH-value of the peroxy-containing concentrate of the invention can range from about 0 to 7 and preferably from 0.5 to 5.

Throughout the specification the term "perglutaric acid" refers to monoperoxyglutaric acid, diperoxyglutaric acid or mixtures thereof. Thus it will be understood that the peroxy-containing concentrate of the invention can contain monoperoxyglutaric acid or diperoxyglutaric acid or mixtures thereof.

Perglutaric acid is readily prepared by well known procedures. Conveniently, perglutaric acid can be obtained by reacting glutaric anhydride or glutaric acid with aqueous hydrogen peroxide, or by treating the peroxide of perglutaric acid with aqueous hydrogen peroxide or water. The peroxide of glutaric acid has the formula $$HOOC\text{-}CH_2CH_2CH_2CO\text{-}O\text{-}O\text{-}COCH_2CH_2CH_2COOH$$

which is obtained on reaction of glutaric anhydride with hydrogen peroxide.

The peroxy-containing concentrates of the invention are conveniently prepared by combining glutaric anhydride and aqueous hydrogen peroxide solution and stirring the resulting mixture until a clear solution is obtained. The amounts of glutaric anhydride, hydrogen peroxide and water employed are selected such that their concentrations in the resulting concentrate meet the weight-percent requirements defined hereinbefore. The appropriate amount of the stabilizing agent can be added prior to or after completion of the reaction.

The peroxy-containing concentrate of the invention also can be prepared by dissolving monoperglutaric acid or diperglutaric acid or mixtures thereof and a stabilizing agent in aqueous hydrogen peroxide in amounts which will result in a concentrate containing the appropriate weight-percent concentrations of these ingredients as defined hereinbefore.

As is well known, in aqueous solution, percarboxylic acids and water exist in equilibrium with hydrogen peroxide and the corresponding carboxylic acid. Therefore, the peroxy-containing concentrates of this invention inherently will contain some glutaric acid.

A comparison of perglutaric acid solutions, persuccinic acid solutions and permaleic acid solutions, the results of which are more fully described hereinbelow, with and without a stabilizing agent, each prepared by reacting the corresponding anhydride with 35% aqueous hydrogen peroxide, demonstrated not only that the highest peracid concentrations are obtained with perglutaric acid but that the perglutaric acid solutions have superior stability. In making the comparison, it was noted that the highest attainable concentrations of perglutaric acid, persuccinic acid and permaleic acid were obtained when the corresponding anhydrides and aqueous hydrogen peroxide solution were reacted in the following proportions by weight (grams):

succinic anhydride/35% $H_2O_2$ = 6/100
maleic anhydride/35% $H_2O_2$ = 25/100
glutaric anhydride/35% $H_2O_2$ = 55/100

An increase in the amounts of anhydride over those noted above resulted in partial crystallization on standing a few days.

Aqueous percarboxylic acid solutions were prepared by reacting the following:

(1) 5 g. succinic anhydride and 95 g. 35% $H_2O_2$
(2) 20 g. maleic anhydride and 80 g. 35% $H_2O_2$
(3) 20 g. glutaric anhydride and 80 g. 35% $H_2O_2$ The resulting solutions were allowed to stand and were assayed periodically for hydrogen peroxide (ceric sulfate titration) and percarboxylic acid (iodometrically). The concentrations of percarboxylic acid were calculated on the basis of monoperoxy acid. The results are tabulated in Table 1.

Table 1

| Solution | Time in days | Wt. % $H_2O_2$ | Wt. % Monoperoxyacid |
|---|---|---|---|
| | 15 | 33.4 | 5.6 |
| 1 | 76 | 32.8 | 3.7 |
| | 167 | 31.0 | 3.4 |
| | 20 | 26.4 | 9.8 |
| 2 | 123 | 21.9 | 3.6 |
| | 207 | 18.5 | 2.1 |
| | 36 | 21.3 | 12.9 |
| 3 | 72 | 17.9 | 10.3 |
| | 100 | 15.0 | 8.0 |

Additional percarboxylic acid solutions were prepared from 10 and 20 parts of maleic anhydride (MA), succinic anhydride (SA) and glutaric anhydride (GA) and the remainder to 100 parts 35% $H_2O_2$. The solutions were assayed for percarboxylic acid periodically over a 31-day period. The results are given in Table 2.

Table 2

| Starting Anhydride | Wt.-% Of Percarboxylic Acid Time (days) | | | | |
|---|---|---|---|---|---|
| (parts) | 0 | 3 | 10 | 18 | 31 |
| MA (10) | 9.97 | 3.90 | 2.91 | 3.35 | 2.88 |
| Sa (10) | | 11.07 | 9.36 | 8.53 | 7.35 |
| GA (10) | | 10.74 | 10.73 | 9.85 | 8.64 |
| MA (20) | 20.24 | 7.58 | 6.40 | 6.66 | 5.80 |
| SA (20) | | 19.71 | 16.90 | 13.84 | 9.46 |
| GA (20) | | 20.02 | 17.92 | 15.03 | 12.63 |

The underlined values in Table 2 (and Tables 3 and 4 below) indicate the onset of crystallization.

Percarboxylic acid solutions were prepared from 10 and 20 parts of maleic anhydride, succinic anhydride and glutaric anhydride, 0.2 part of a stabilizing agent, and the remainder to 100 parts 35% $H_2O_2$. The solutions were allowed to stand for an extended period of time and were assayed periodically for percarboxylic acid. The results are given in Tables 3 and 4.

Table 3

| Starting Anhydride | (0.2 parts of urea as stabilizing agent) Wt.-% Of Percarboxylic Acid Time (days) | | | | |
|---|---|---|---|---|---|
| (parts) | 0 | 3 | 10 | 18 | 31 |
| MA (10) | 10.68 | 3.48 | 3.45 | 3.4 | 3.80 |
| SA (10) | | 11.36 | 8.85 | 7.59 | 6.12 |
| GA (10) | | 11.07 | 10.69 | 9.76 | 9.48 |
| MA (20) | 19.95 | 7.26 | 6.75 | 6.08 | 5.15 |
| SA (20) | | 20.92 | 18.18 | 15.55 | 12.17 |
| GA (20) | | 20.39 | 20.82 | 19.98 | 19.22 |

Table 4

| Starting Anhydride | (0.1 part 2,3-pyridinedicarboxylic acid + 0.1 part 2,6-pyridinedicarboxylic acid as stabilizer) Wt.-% Of Percarboxylic Acid Time (days) | | | | | |
|---|---|---|---|---|---|---|
| (parts) | 0 | 3 | 10 | 18 | 31 | 108 |
| MA (10) | 10.60 | 3.48 | 4.06 | 3.51 | 3.27 | |
| SA (10) | | 11.04 | 9.69 | 8.56 | 7.82 | |
| GA (10) | | 10.77 | 10.53 | 10.86 | 10.50 | 8.16 |
| MA (20) | 19.72 | 8.27 | 7.03 | 6.82 | 6.31 | |
| SA (20) | | 22.20 | 18.60 | 13.77 | 10.29 | |

Table 4-continued

| Starting Anhydride (parts) | (0.1 part 2,3-pyridinedicarboxylic acid + 0.1 part 2,6-pyridinedicarboxylic acid as stabilizer) Wt.-% Of Percarboxylic Acid Time (days) 0 | 3 | 10 | 18 | 31 | 108 |
|---|---|---|---|---|---|---|
| GA (20) | | 20.21 | 20.00 | 19.6 | 19.35 | |

The perglutaric acid solutions were found to be less corrosive than the persuccinic acid solutions and less toxic than the permaleic acid solutions.

Even solutions having a high perglutaric acid content were found to be surprisingly stable. Thus a concentrate was prepared from 55 parts of glutaric anhydride, 0.1 part 2,3-pyridinedicarboxylic acid, 0.1 part 2,6-pyridinedicarboxylic acid and the remainder 35% aqueous hydrogen peroxide solution to 100 parts. The resulting concentrate was colorless and odorless. The concentrate was allowed to stand one month at room temperature and assayed after 14 days for 6.54% hydrogen peroxide and 41.24% perglutaric acid; and after 30 days for 6.46% hydrogen peroxide and 39.13% perglutaric acid.

The peroxy-containing concentrates of the invention are miscible with water and water-miscible organic solvents such as acetone and ethyl alcohol. On mixing the concentrate with water-immiscible organic solvents such as chloroform, methylene dichloride, benzene, ethyl acetate and ether, the perglutaric acid can be extracted into the organic phase.

An advantage of the peroxy-containing concentrates of the invention is that they can be mixed with a large number of oxidation-stable substances, without adversely affecting their stability or percarboxylic acid content, in order to improve their use properties. For example, inorganic acids such as sulfuric acid or phosphoric acid can be added to adjust the pH of the concentrate. Perfumes can be added to impart a desired odor to the concentrate and surfactants can be added to reduce the surface tension or to produce a foaming product. Suitable surfactants are nonionic, anionic and cationic wetting agents, betaines, amine oxides such as dimethyldodecylamine oxide, and phosphine oxides, such as dimethyldodecylphosphine oxide.

Perglutaric acid decomposes to glutaric acid under certain conditions. For example, it decomposes gradually in very dilute solution, or more rapidly through the catalytic action of noble metals or of enzymes or catalytically active materials present in waste water. Glutaric acid is a naturally occurring compound and accordingly poses no residue problems.

The peroxy-containing concentrates of this invention can be used for disinfection purposes, e.g., in the food industry, for ion exchangers, circulation water, air conditioning systems, for disinfection of medical and dental instruments, for disinfection of utensils in hospitals, etc. They are further useful for oxidation and bleaching purposes and are excellent replacements for peracetic acid presently employed for these purposes.

The bacteriological activity of the peroxy-containing concentrates of the invention and their spectrum of activity is set forth in Table 5.

The minimum inhibitory concentrations (MIC) as well as bactericidal and fungicidal activity in suspension, surface and germ carrier tests were determined in accordance with the Richtlinien für die Prüfung chemischer Desinfektionsmittel, 3. Aufl., Gustav-Fischer Verlag, Stuttgart (Guidelines for the Testing of Chemical Disinfectants, 3rd. Edition, Gustav-Fischer Publishers, Stuttgart).

Table 5

Bacteriological Activity

Concentrate 10 parts glutaric anhydride
0.1/0.1 parts 2,3/2,6-pyridinedicarboxylic acids
add to 100 parts 35% $H_2O_2$ Suspension, Bacteria - without presence of serum (killing time in minutes)

| Conc. | *Staphylococcus aureus* | *Klebsiella pneumoniae* | Pseudomonas *aeruginosa* | *Proteus vulgaris* |
|---|---|---|---|---|
| 0.05% | 5 | 15 | 5 | 2½ |
| 0.1% | 5 | 2½ | 2½ | 2½ |
| 0.25% | 2½ | 2½ | 2½ | 2½ |

Suspension, Bacteria - in presence of 20% serum (killing time in minutes)

| Conc. | *Staphylococcus aureus* | *Klebsiella pneumoniae* | *Pseudomonas aeruginosa* | *Proteus vulgaris* |
|---|---|---|---|---|
| 0.25% | >30 | >30 | >30 | 30 |
| 0.5% | 2½ | 2½ | 15 | 2½ |
| 1.0% | 2½ | 2½ | 2½ | 2½ |

Suspension, Fungi (killing time in minutes)

| Conc. | *Trichophyton mentagrophytes* | *Candida albicans* | *aspergillus niger* |
|---|---|---|---|
| 0.5% | >30 | >30 | >30 |
| 1.0% | 15 | >30 | >30 |
| 2.0% | 15 | 30 | >30 |

Spores, Germ Carrier: Bohemian Garnets (killing time in hours)

| Concentration | *Bacillus subtilis* |
|---|---|
| 0.1% | 6 |
| 0.25% | 3 |
| 0.5% | 1 |

Tuberclebacilli, Germ Carrier: Cambric (killing time in minutes)

| Concentration | *Mycobacterium smegmatis* |
|---|---|
| 1% | >120 |

Activity on Surfaces, Surface PVC (killing time in hours)

| Concentration | *Staphylococcus aureus* | *Escheria coli* |
|---|---|---|
| 0.25% | >6 | >6 |
| 0.5% | >6 | 1 |
| 1.0% | 1 | 1 |

Minimum Inhibitory Concentration (series dilution test)

| *Staphylococcus aureus* | *Klebsiella pneumoniae* | *Pseudomonas* aeruginosa | *Proteus vulgaris* |
|---|---|---|---|
| ≦0.05 | ≦0.05 | ≦0.05 | ≦0.05 |
| *Trichophyton mentagrophytes* | *candida albicans* | *Aspergillus niger* | |
| ≦0.05 | 0.5 | 0.5 | |

We claim:

1. A stable, aqueous peroxy-containing concentrate consisting essentially of by weight of the concentrate:
(a) about 1 to 60 percent of perglutaric acid;
(b) about 1 to about 50 percent of hydrogen peroxide;
(c) about 0.01 to about 2 percent of a stabilizing agent for the perglutaric acid and the hydrogen peroxide; and (d) the remainder to 100 percent water.

2. A peroxy-containing concentrate according to claim 1 wherein the stabilizing agent is selected from the group consisting of urea, pyridine N-oxide, 2,3-pyridinedicarboxylic acid, 2,6-pyridinedicarboxylic acid and a mixture of 2,3-pyridinedicarboxylic acid and 2,6-pyridinedicarboxylic acid.

3. A peroxy-containing concentrate according to claim 2 wherein the stabilizing agent is present in an amount of about 0.01 to about 0.2 percent by weight of the concentrate.

* * * * *

UNITED STATES PATENT AND TRADEMARK OFFICE

CERTIFICATE OF CORRECTION

PATENT NO. : 4,129,517

DATED : December 12, 1978

INVENTOR(S) : Heinz Eggensperger and Wolfgang Beilfuss

It is certified that error appears in the above-identified patent and that said Letters Patent are hereby corrected as shown below:

Column 4, Table 1, should read

-- Table 1 --.

| Solution | Time in days | Wt. % $H_2O_2$ | Wt. % Monoperoxyacid |
|---|---|---|---|
| 1 | 15 | 33.4 | 5.6 |
| | 76 | 32.8 | 3.7 |
| | 167 | 31.0 | 3.4 |
| 2 | 20 | 26.4 | 9.8 |
| | 123 | 21.9 | 3.6 |
| | 207 | 18.5 | 2.1 |
| 3 | 36 | 21.3 | 12.9 |
| | 72 | 17.9 | 10.3 |
| | 100 | 15.0 | 8.0 |

UNITED STATES PATENT AND TRADEMARK OFFICE

CERTIFICATE OF CORRECTION

PATENT NO. : 4,129,517

DATED : December 12, 1978

INVENTOR(S) : Heinz Eggensperger and Wolfgang Beilfuss

It is certified that error appears in the above-identified patent and that said Letters Patent are hereby corrected as shown below:

Column 4, Table 2, should read

-- Table 2

| Starting Anhydride (parts) | Wt.-% Of Percarboxylic Acid Time (days) 0 | 3 | 10 | 18 | 31 |
|---|---|---|---|---|---|
| MA (10) | 9.97 | 3.90 | 2.91 | 3.35 | 2.88 |
| SA (10) | | 11.07 | 9.36 | 8.53 | 7.35 |
| GA (10) | | 10.74 | 10.73 | 9.85 | 8.64 |
| MA (20) | 20.24 | 7.58 | 6.40 | 6.66 | 5.80 |
| SA (20) | | 19.71 | 16.90 | 13.84 | 9.46 |
| GA (20) | | 20.02 | 17.92 | 15.03 | 12.63 |

--.

UNITED STATES PATENT AND TRADEMARK OFFICE
CERTIFICATE OF CORRECTION

PATENT NO. : 4,129,517

DATED : December 12, 1978

INVENTOR(S) : Heinz Eggensperger and Wolfgang Beilfuss

It is certified that error appears in the above-identified patent and that said Letters Patent are hereby corrected as shown below:

Column 4, Table 3, should read

-- Table 3 --

(0.2 parts of urea as stabilizing agent)

| Starting Anhydride (parts) | Wt.-% Of Percarboxylic Acid Time (days) 0 | 3 | 10 | 18 | 31 |
|---|---|---|---|---|---|
| MA (10) | 10.68 | 3.48 | 3.45 | 3.4 | 3.80 |
| SA (10) | | 11.36 | 8.85 | 7.59 | 6.12 |
| GA (10) | | 11.07 | 10.69 | 9.76 | 9.48 |
| MA (20) | 19.95 | 7.26 | 6.75 | 6.08 | 5.15 |
| SA (20) | | 20.92 | 18.18 | 15.55 | 12.17 |
| GA (20) | | 20.39 | 20.82 | 19.98 | 19.22 |

UNITED STATES PATENT AND TRADEMARK OFFICE

CERTIFICATE OF CORRECTION

PATENT NO. : 4,129,517

DATED : December 12, 1978

INVENTOR(S) : Heinz Eggensperger and Wolfgang Beilfuss

It is certified that error appears in the above-identified patent and that said Letters Patent are hereby corrected as shown below:

Columns 4-5, Table 4, should read

-- Table 4

(0.1 part 2,3-pyridinedicarboxylic acid + 0.1 part 2,6-pyridinedicarboxylic acid as stabilizer)

| Starting Anhydride (parts) | Wt.-% Of Percarboxylic Acid Time (days) | | | | | |
|---|---|---|---|---|---|---|
| | 0 | 3 | 10 | 18 | 31 | 108 |
| MA (10) | 10.60 | 3.48 | 4.06 | 3.51 | 3.27 | |
| SA (10) | | 11.04 | 9.69 | 8.56 | 7.82 | |
| GA (10) | | 10.77 | 10.53 | 10.86 | 10.50 | 8.16 |

--.

UNITED STATES PATENT AND TRADEMARK OFFICE
CERTIFICATE OF CORRECTION

PATENT NO. : 4,129,517

DATED : December 12, 1978

INVENTOR(S) : Heinz Eggensperger and Wolfgang Beilfuss

It is certified that error appears in the above-identified patent and that said Letters Patent are hereby corrected as shown below:

Table 4-continued (0.1 part 2,3-pyridinedicarboxylic acid + 0.1 part 2,6-pyridinedicarboxylic acid as stabilizer)

| Starting Anhydride (parts) | Wt.-% Of Percarboxylic Acid Time (days) | | | | | |
|---|---|---|---|---|---|---|
| | 0 | 3 | 10 | 18 | 31 | 108 |
| MA (20) | 19.72 | 8.27 | 7.03 | 6.82 | 6.31 | |
| SA (20) | | 22.20 | 18.60 | 13.77 | 10.29 | |
| GA (20) | | 20.21 | 20.00 | 19.6 | 19.35 | |

Signed and Sealed this

*Tenth* Day of *April 1979*

[SEAL]

*Attest:*

RUTH C. MASON
*Attesting Officer*

DONALD W. BANNER
*Commissioner of Patents and Trademarks*